United States Patent [19]

Dukowski

[11] Patent Number: 4,478,216
[45] Date of Patent: Oct. 23, 1984

[54] PORTABLE AIR FILTRATION DEVICE

[75] Inventor: Hubert G. Dukowski, North Vancouver, Canada

[73] Assignee: H.G.D. Enterprises Ltd., Vancouver, Canada

[21] Appl. No.: 368,024

[22] Filed: Apr. 13, 1982

[30] Foreign Application Priority Data

Apr. 6, 1982 [CA] Canada ................................. 400573

[51] Int. Cl.³ ............................................. A62B 7/10
[52] U.S. Cl. ........................... 128/204.21; 128/205.12; 55/DIG. 35; 55/482; 55/471; 415/121 G; 415/203
[58] Field of Search ...................... 128/204.21, 205.12, 128/205.25, 205.29, 206.15, 206.17, 201.28; 55/469, 471, 482, DIG. 35, DIG. 33, 419; 415/121 R, 121 G, 203; 2/171.3; 98/43 B

[56] References Cited

U.S. PATENT DOCUMENTS 3,657,740  4/1972  Cialone ........................ 128/205.25
4,233,972  11/1980  Hauff et al. .................... 128/205.12
4,320,755  3/1982  Flint et al. ..................... 128/204.21

FOREIGN PATENT DOCUMENTS 2032284  5/1980  United Kingdom ........... 128/201.25

Primary Examiner—Henry J. Recla
Attorney, Agent, or Firm—Sim & McBurney

[57] ABSTRACT

There is provided a portable breathing assist comprising an external housing and an internal scroll housing within the external housing. The scroll housing has a central inlet for air and a tangential outlet for air. A radial impeller is rotatably mounted within the scroll housing for moving air from the inlet to the outlet, and an electrical motor within the external housing but outside the scroll housing rotates the impeller. An air manifold within the external housing is provided to define a passageway for air from at least one opening to a central inlet, along which air can travel without encountering the electrical motor. Filter means are provided at the at least one opening.

3 Claims, 3 Drawing Figures

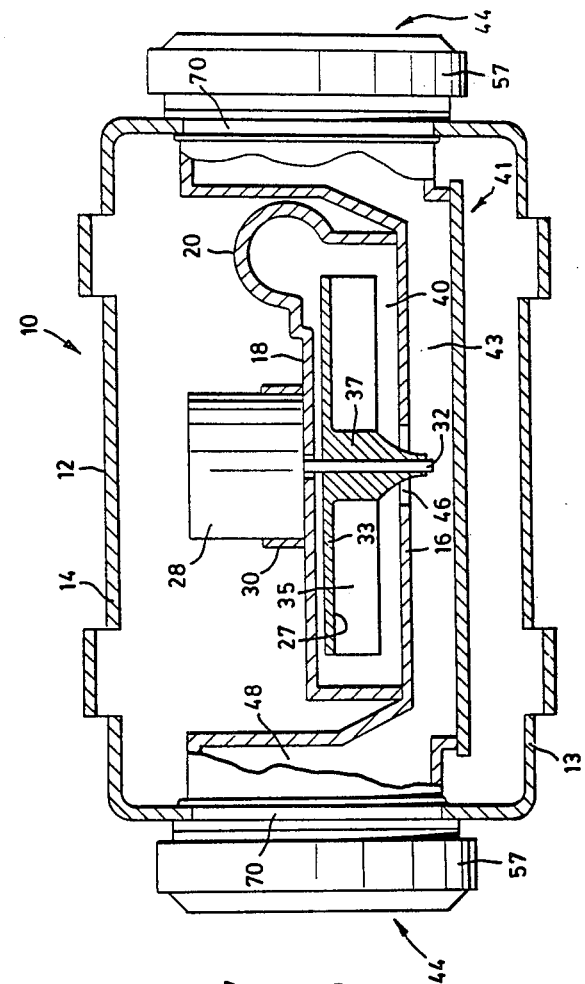
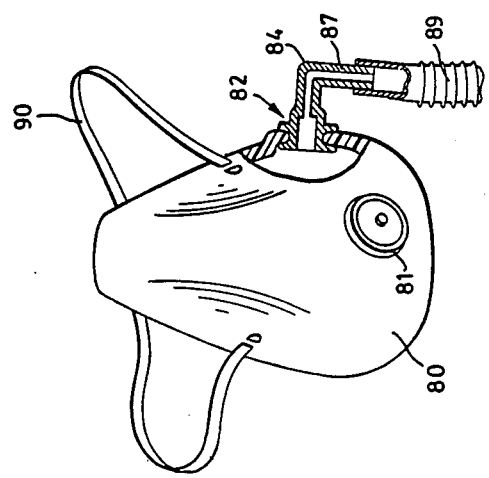
FIG. 2
FIG. 3

PORTABLE AIR FILTRATION DEVICE

This invention relates general to portable breathing assist devices, and has to do particularly with a portable breathing assist of improved construction.

BACKGROUND OF THE INVENTION

Portable breathing assists are already known. Prior art devices tend to utilize a fan means driven by an electrical motor, filter media usually upstream of the fan means, and a breathing mask downstream of the fan. Aside from the inefficiency of the fan as an air mover, the prior art generally tends to suffer from a lack of compactness in design, and an unduly complicated structure which increases the cost of the item. Exemplary of the prior art are the following patents: U.S. Pat. No. 4,127,122, issued Nov. 28, 1978 to Kienhofer et al.; U.S. Pat. No. 2,332,662, issued Oct. 26, 1943 to Nathanson; U.S. Pat. No. 3,620,213, issued Nov. 16, 1971 to Savoie; U.S. Pat. No. 3,736,927, issued June 5, 1973 to Misaqi; U.S. Pat. No. 2,881,758, issued Apr. 14, 1959 to Motsinger; and U.S. Pat. No. 4,233,972, issued Nov. 18, 1980 to Hauff et al.

SUMMARY OF THE INVENTION

In view of the disadvantages of the prior art apparatus, the present invention provides a portable breathing assist, which includes an external housing and an internal scroll housing within the external housing. The scroll housing has a central inlet for air and a tangential outlet for air, and a radial impeller is rotatably mounted within the scroll housing for moving air from the inlet to the outlet. An electrical motor within the external housing but outside the scroll housing is provided for rotating the impeller, and an air manifold within the external housing defines a passageway for air from two openings to the central inlet. Along this passageway, air can travel without encountering the electrical motor. The two openings include filter means, and the air manifold includes an inner plate having the central inlet therethrough. A cup-like member co-operates with the inner plate on one side thereof to define the scroll housing, while two side plates and an outer plate co-operate with the inner plate on the other side thereof to provide the manifold defining the passageway. The motor is located on the other side of the cup-like member from the inner plate.

By arranging the structure such that air in the passageway does not encounter the electrical motor, no problems arise relating to the ionization of air prior to being breathed. Also, the smell arising from an electrical motor in operation is not passed into the lungs of the user.

BRIEF DESCRIPTION OF THE DRAWINGS

One embodiment of this invention is illustrated in the accompanying drawings, in which like numerals denote like parts throughout the several views, and in which:

FIG. 2 is a sectional view taken along the line 2—2 in FIG. 1, with the breathing assist assembled together; and FIG. 3 is a perspective view of a breathing mask for use with the portable breathing assist.

DETAILED DESCRIPTION OF THE DRAWINGS

Figure 1:
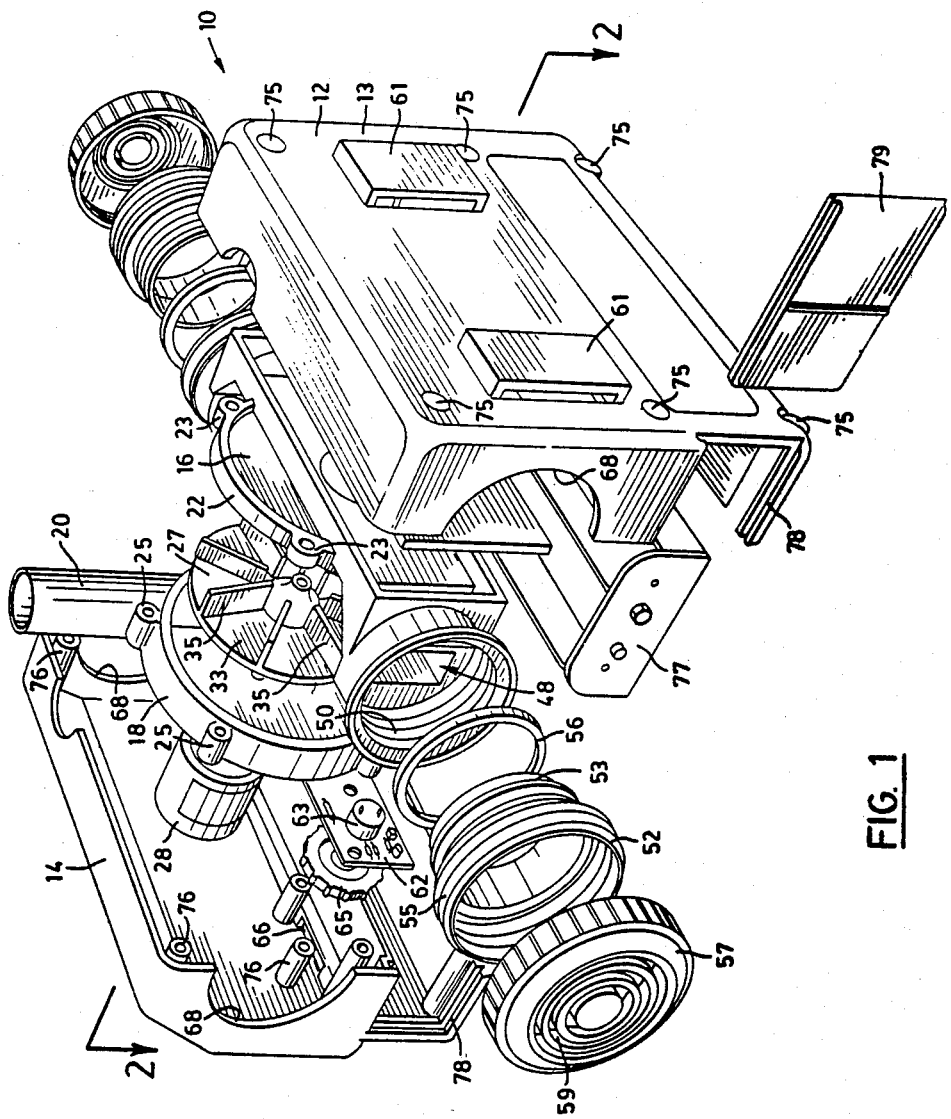
FIG. 1 is an exploded perspective view of a portable breathing assist constructed in accordance with this invention.

Attention is first directed to FIG. 1, which shows a portable breathing assist 10, including a two part external housing 12 comprising a first half 13 and a second half 14. The breathing assist 10 further includes an internal scroll housing which is defined between an inner plate 16 and a cup-like member 18 which cooperates with the inner plate. The cup-like member 18 includes a tangential outlet pipe 20 in the usual manner of impeller designs.

The inner plate 16 has a rim 22 which includes four ears 23 (only two visible in FIG. 1), each ear 23 being apertured to receive a threaded member which is adapted to thread into a corresponding integral cylinder 25 along the side wall of the cup-like member 18. The inner plate 16 and the cup-like member 18 may be sealed together either with or without a gasket, or may be "solvent-sealed", if both parts are of plastic (as is preferred). In the latter case, the threaded fasteners would merely hold the parts together during the solvent-sealing.

A radial impeller 27 is provided within the scroll housing defined between the cup-like member 18 and the inner plate 16, the radial impeller being mounted so as to be rotatable centrally of the scroll housing by an electric motor 28 which is snugly received within a cylindrical extension 30 projecting rearwardly from the cup-like member 18. The electric motor 28 supports a shaft 32 on which the radial impeller 27 is mounted. More specifically, looking at FIG. 2, the radial impeller 27 includes a circular plate 33 which supports a plurality of radial blades 35 projecting radially outwardly from a central hub 37 which is snugly mounted on the shaft 32. Thus, energization of the electric motor 28 will cause rotation of the radial impeller 27 within the scroll housing 40 defined between the cup-like member 18 and the inner plate 16.

An air manifold shown generally by the numeral 41 is provided within the external housing 12, and defines a passageway 43 for air from two openings 44 to a central inlet 46 into the internal scroll housing defined between the cup-like member 18 and the inner plate 16. Thus, upon rotation of the radial impeller 27, air is drawn in through the openings 44, to and through the inlet 46 into the scroll housing 40, thence radially outwardly to finally exit along the pipe 20.

Looking more specifically at the leftward opening 44 in FIG. 2, and the nearer equivalent structure in FIG. 1, it will be seen that the air passageway 43 communicates with a plenum 48 which communicates directly with a circular threaded opening 50 adapted to receive an externally threaded component 52 having a portion 53 of smaller diameter and a portion 55 of larger diameter. The portion 53 of smaller diameter is adapted to thread into the threaded opening 50, and the shoulder between the portions 53 and 55 is adapted to compress a gasket or sealing ring 56 against the outside of the threaded opening 50. A cap 57 in internally threaded and is adapted to be screwed onto the portion 55 of the component 52, the cap 57 containing a filter pad 59 (partially seen through the grille of the cap 57).

The identical structure exists at the other end (the other opening 44), and the description does not need to be repeated.

As can be seen in FIG. 2, the design of the various components is such that the motor 28 does not require a protruding portion of the housing in order to encompass it. More specifically, it can be seen in FIG. 2 that the passageway 43 and the scroll housing 40 are displaced to one side with respect to a centre line through the openings 44, such that the motor 28 is substantially contained within a hypothetical extension of the two circular openings 44. Thus, the housing 12 can be made as small as possible, and free from protrusions or bumps.

Returning to FIG. 1, the housing half 13 has brackets 61 to allow a belt to be threaded therethrough, the belt being intended to secure the device shown in FIG. 1 around the waist of the user.

Also in FIG. 1, the other housing half 14 is seen to include an electrical mounting board 62 supporting, inter alia, a potentiometer 63 which is electrically wired to control the energy being fed to the electrical motor 28, more particularly to control the voltage being fed to the electrical motor. The potentiometer 63 is controlled by a knob 65 a portion of which projects downwardly through a slot 66 in the housing half 14, so that access may be had to the knob 65 from the outside of the housing when it is closed together.

As can also be seen in FIG. 1, each housing half 13 and 14 has two semi-circular recesses 68, one at either end, which are adapted to cooperate with a recess 70 defined on the outside of the threaded opening 50 (see FIG. 2). This locks the scroll and manifold in place with respect to the rest of the housing, and means that, in order to disassemble the various parts, all that is necessary is to release the two housing halves from one another by removing screws (not shown) which pass through a series of openings 75 in the rightward housing half 13 in FIG. 1, and enter bored cylinders 76 in the other housing half 14, in known fashion.

The housing half 13 may contain a battery pack (in holder 77) which powers the electric motor 28. Alternatively, the electric motor 28 may be powered from a wall outlet by incorporating the use of a standard AC/DC rectifier. As a further variant, the electrical connections can be made so that the electric motor 28 can draw power from either source, selectively.

A doorway 78 extending across the lower portion of both housing halves 13 and 14 cooperates with a sliding door 79 so as to permit the battery pack to be removed or replaced.

Attention is now directed to FIG. 3, which shows a standard face mask 80 having an exhalation exhaust valve 81, and an opening 82 for an inlet. In many of the simpler types of face masks, a filter arrangement is applied directly to the opening 82, and the wearer simply draws air in through the filter media, and of course must expend energy in doing so. To adapt the face mask of FIG. 3 for use with the portable breathing assist shown in FIGS. 1 and 2 of the drawings, an adaptor 84 is provided. The adaptor 84 includes a spool portion 86 connected to an elbow portion 87, the elbow portion 87 being cooperable with the end of a flexible hose 89, the other end of which is adapted to be connected directly to the pipe 20 (see FIG. 1). As can be seen, the spool portion 86 snugly receives the edges of the opening 82 in the face mask 80, and it will be appreciated that, once in place as shown in FIG. 3, the elbow portion 87 could be swivelled back and forth.

If desired, the spool portion 86 could include a one-way flap valve of known type which allows air to enter the face mask, but not be breathed out of the face mask and into the adaptor 84.

The face mask includes the usual strap 90 to secure it around the head of the user.

Some face masks have more than one inlet of a conventional variety, and in order to adapt these double inlet face masks for use with the portable breathing assist shown in FIGS. 1 and 2, the other inlet would be either blocked off or converted to an exhalation exhaust portion similar to that shown at 81 in FIG. 3. This would be done by the use of a standard exhaust valve kit available from the manufacturer of the face mask.

I claim:

1. A portable breathing assist comprising:
   an external housing,
   an internal scroll housing within the external housing, the scroll housing comprising a central plate mounted in said external housing and having a central inlet for air and a cup-like member having a tangential outlet for air mounted to said central plate concentrically with said central inlet, said tangential outlet extending through said external housing as well, breathing tube means connected to said outlet;
   a radial impeller rotatably mounted within the scroll housing for moving air from said inlet to said outlet,
   an electrical motor within said external housing but outside said scroll housing and having means connected to said impeller for rotating the same,
   the external housing defining at least one opening,
   filter means mounted over said at least one opening for filtering all air passing therethrough;
   air manifold means within said external housing, the air manifold defining a passageway for air from said at least one opening to said central inlet, along which air can travel without encountering said electrical motor, said air manifold means having a first portion of rectangular cross-section comprised of said inner plate having said central inlet therethrough, two substantially parallel side plates connected perpendicularly to said inner plate and an outer plate substantially parallel with said inner plate and connected to said side plates, said air manifold means having a second portion comprised of conduit means fluidically connecting said at least one opening to said first portion, the said motor being located on the other side of the cup-like member from the inner plate.

2. The invention claimed in claim 1, which further includes means for variably adjusting the speed of rotation of the motor and impeller.

3. The invention claimed in claim 1 or claim 2, which further includes a battery means for powering the electrical motor.

* * * * *